US012714306B2

(12) United States Patent
Tripathi et al.

(10) Patent No.: US 12,714,306 B2
(45) Date of Patent: Aug. 25, 2026

(54) OBTAINING OPHTHALMIC INFORMATION USING MULTICOLOR ENDOILLUMINATION WITH HYPERSPECTRAL IMAGING

(71) Applicant: Alcon Inc., Fribourg (CH)

(72) Inventors: Ashok Burton Tripathi, Santa Barbara, CA (US); John Park, Irvine, CA (US); Qing Xiang, Irvine, CA (US)

(73) Assignee: Alcon Inc., Fribourg (CH)

(*) Notice: Subject to any disclaimer, the term of this patent is extended or adjusted under 35 U.S.C. 154(b) by 839 days.

(21) Appl. No.: 18/065,425

(22) Filed: Dec. 13, 2022

(65) Prior Publication Data

US 2023/0190098 A1 Jun. 22, 2023

Related U.S. Application Data

(60) Provisional application No. 63/290,538, filed on Dec. 16, 2021.

(51) Int. Cl.
*A61B 3/14* (2006.01)
*G01J 3/28* (2006.01)

(52) U.S. Cl.
CPC .............. *A61B 3/14* (2013.01); *G01J 3/2823* (2013.01)

(58) Field of Classification Search
CPC ........... A61B 3/14; A61B 3/12; A61B 5/0075; A61B 5/0086; A61B 5/14546;
(Continued)

(56) References Cited

U.S. PATENT DOCUMENTS 7,246,905 B2 7/2007 Benedikt
9,185,357 B2 11/2015 Boccara
(Continued)

FOREIGN PATENT DOCUMENTS

CN 112816420 A 5/2021
WO 9916353 A1 4/1999
(Continued)

OTHER PUBLICATIONS

Ayon Dey, Machine learning algorithms: a review, International jurnal of computer science and information technologies, vol. 7, pp. 1174-1179, 2016.
(Continued)

*Primary Examiner* — Matthew Y Lee

(57) ABSTRACT

In certain embodiments, a system for obtaining ophthalmic information includes an illumination device having an optical fiber; a hyperspectral illumination source; a controller; a modulation device; and an imaging device. The modulation device is configured to receive first source light generated from the hyperspectral illumination source. The first source light includes multiple wavelengths. The modulation device is also configured to modulate each of the wavelengths with a different frequency to generate second source light having multiple frequency modulated wavelengths, and transmit the second source light to an optical fiber, which emits the second source light to contact an eye tissue. The imaging device selects a first frequency associated with a first frequency modulated wavelength and captures light returning from the eye tissue as a result of the first frequency modulated wavelength contacting the eye tissue. The controller determines parameter(s) of the eye tissue based on the return light.

20 Claims, 7 Drawing Sheets

(58) Field of Classification Search

CPC ......... A61B 5/7257; A61B 1/043; A61B 3/10; A61B 3/102; A61B 5/0071; A61B 5/1455; A61B 5/742; A61B 1/00165; A61B 1/0638; A61B 351/21; A61B 351/221; A61B 351/211; A61B 5/00; A61B 5/145; A61B 1/00; G01J 3/2823; G01J 2003/2826; G01J 3/28; G01J 3/42; G01J 2003/104; G01J 3/0218; G01J 3/10; G01J 3/108; G01J 3/26; G01J 3/4406; G01J 3/453; G01J 3/02

See application file for complete search history.

(56) References Cited

U.S. PATENT DOCUMENTS

| | | | | |
|---|---|---|---|---|
| 2004/0085542 | A1* | 5/2004 | Soliz | G01J 3/2823 356/456 |
| 2006/0140497 | A1 | 6/2006 | Kondo et al. | |
| 2007/0156021 | A1* | 7/2007 | Morse | A61B 1/0692 600/176 |
| 2010/0085537 | A1 | 4/2010 | Ramella-roman et al. | |
| 2012/0065518 | A1 | 3/2012 | Mangoubi | |
| 2013/0128227 | A1 | 5/2013 | Cui et al. | |
| 2014/0002793 | A1 | 1/2014 | Hogan | |
| 2014/0276025 | A1 | 9/2014 | Durbin | |
| 2014/0300864 | A1 | 10/2014 | Fukuma | |
| 2015/0015692 | A1* | 1/2015 | Smart | G01J 3/2823 348/77 |
| 2016/0278678 | A1* | 9/2016 | Valdes | A61B 5/14546 |
| 2016/0338588 | A1* | 11/2016 | Friedman | A61K 31/525 |
| 2016/0360958 | A1 | 12/2016 | Tsuri | |
| 2017/0042464 | A1 | 2/2017 | Verdooner | |
| 2017/0059408 | A1* | 3/2017 | Körner | G01J 3/0229 |
| 2017/0176336 | A1 | 6/2017 | Dimitriadis et al. | |
| 2017/0297144 | A1 | 10/2017 | Nakanishi | |
| 2018/0136486 | A1 | 5/2018 | Macnamara | |
| 2019/0298170 | A1* | 10/2019 | Artal Soriano | A61B 3/0008 |
| 2019/0343384 | A1 | 11/2019 | Plaian | |
| 2019/0388271 | A1* | 12/2019 | Abt | A61B 3/13 |
| 2021/0169324 | A1* | 6/2021 | Tripathi | H04N 13/156 |
| 2022/0151568 | A1 | 5/2022 | Yao | |
| 2022/0157470 | A1 | 5/2022 | Sylvestre | |
| 2022/0160228 | A1 | 5/2022 | Leahy et al. | |
| 2022/0225877 | A1 | 7/2022 | Shiba et al. | |
| 2022/0240779 | A1* | 8/2022 | Peyman | A61B 5/0066 |
| 2022/0260413 | A1 | 8/2022 | Perruchot et al. | |
| 2023/0018494 | A1 | 1/2023 | Gribble et al. | |
| 2024/0415383 | A1 | 12/2024 | Shaked et al. | |
| 2025/0150564 | A1 | 5/2025 | Mizutani et al. | |

FOREIGN PATENT DOCUMENTS

| | | | |
|---|---|---|---|
| WO | 2015023990 | A1 | 2/2015 |
| WO | 2020047594 | A1 | 3/2020 |
| WO | 2021151046 | A1 | 7/2021 |
| WO | 2022011420 | A1 | 1/2022 |
| WO | 2022153320 | A1 | 7/2022 |

OTHER PUBLICATIONS

Chen Qingyu et al., Multi-modal, multi-task, multi-attention (M3) deep learning detection of regular pseudodrusen: towards automated accessible classification of age-related macular degeneration, pp. 1-31, 2020URL:https://arxiv.org/abs/2011.05142vl.

Citation: M. Arsalan et al., Segmenting Retinal Vessels Using a Shallow Segmentation Network to Aid Ophthalmic Analysis, Mathematics, vol. 10, p. 1536, 2022.

J. Fhima et al., PVBM: A Python Vasculature Biomarker Toolbox Based on Retinal Blood Vessel Segmentation, Cornell University, 2022.

Sarraf David et al.,Retinal pigment epithelial tears in the era of intravitreal pharmacotherapy: risk factors, pathogenesis, prognosis and treatment (an American Ophthalmological Society thesis), American Ophthalmological Society, Transactions, vol. 112, pp. 142-159, 2014.

Yonlong He, et al., Segmenting Diabetic Retinopathy Lesions in Multispecial Images Using Low-Dimensional Spatial-Spectral Matrix Representation, Ieee Juournal of Biomedical and helth informatics, Ieee, Piscataway, NJ, USA, vol. 24, No. 2, pp. 493-502, Apr. 20, 2019.

Yoon Jonghee, @Hyperspectrial Imaging for Clinical Applications@ Biochip Journal, Korean Biochip, Seoul, South Korea, vol. 16, No. 1, Jan. 4, 2022, pp. 1-12.

William R. Johnson, Snapshot hyperspectral imaging in ophthalmology, Journal of Biomedical Optics, 12 (1), 014036_1-7, 2007.

* cited by examiner

OBTAINING OPHTHALMIC INFORMATION USING MULTICOLOR ENDOILLUMINATION WITH HYPERSPECTRAL IMAGING

FIELD

Embodiments of the present disclosure generally relate to obtaining ophthalmic information and, more specifically, to systems, devices, and methods for obtaining ophthalmic information with respect to the eye using multicolor endoillumination with hyperspectral imaging.

BACKGROUND

Many microsurgical procedures require precision cutting and/or removal of various body tissues. For example, vitreoretinal procedures such as retinotomies, retinectomies, autologous retinal transplants, and vitrectomies typically require the cutting, removal, dissection, delamination, coagulation, or other manipulation of intraocular tissues such as the retina, vitreous humor, traction bands, and membranes.

Many of these intraocular tissues serve crucial roles in enabling vision. For example, the retina, or the innermost layer lining the back wall of the eye, is responsible for receiving, modulating, and transmitting visual stimuli from the external environment to the optic nerve, and ultimately, the visual cortex of the brain. Structurally, the retina is a complex and delicate tissue with numerous types of cells arranged in multiple cellular layers. Due to the retina's role in vision and its fragility, damage thereto may result in severe loss of vision or even permanent blindness. Therefore, cutting, removal, or other manipulation of the retina should be done with great care to avoid unwanted retinal trauma.

Currently, however, visualization and data acquisition during surgery remain somewhat limited. For example, existing imaging systems lack the capability to provide the surgeon with information measured in situ related to spectral parameters of eye tissues/structures and/or treatment results that could enable real-time adjustment in the use of instruments (e.g., forceps, lasers, probes, etc.) used to manipulate eye tissues/structures during surgery. One exemplary imaging system can generate optical coherence tomography (OCT) images based on scan data from an ophthalmic scanning device. However, identifying areas, structures, and/or tissues of the eye from OCT images poses various challenges due to certain inherent characteristics of OCT images. For example, OCT images may suffer from speckle noise, low signal to noise ratio (SNR), and/or other image interferences that can increase the difficulty in identifying and determining parameters (e.g., thickness, roughness, etc.) of the different structures or tissues of the eye.

Accordingly, it may be beneficial to provide improved systems, devices, and methods for obtaining ophthalmic information associated with various eye tissues/structures during ophthalmic procedures.

SUMMARY

In certain embodiments, a system is provided. The system includes an illumination device comprising an optical fiber, a hyperspectral illumination source, a controller, and a modulation device coupled to each of the illumination device, the hyperspectral illumination source, and the controller. The modulation device is configured to receive first source light generated from the hyperspectral illumination source. The first source light includes a plurality of wavelengths. The modulation device is also configured to modulate each of the plurality of wavelengths of the first source light with a different frequency to generate second source light having a plurality of frequency modulated wavelengths. The modulation device is further configured to transmit the second source light to the optical fiber. The optical fiber is configured to emit the second source light in the optical fiber from the illumination device to illuminate an eye tissue. The first imaging device configured to select at least a first frequency associated with a first frequency modulated wavelength of the plurality of frequency modulated wavelengths of the second source light. The first imaging device is also configured to capture first light returning from the eye tissue as a result of the first frequency modulated wavelength of the second source light contacting the eye tissue. The controller is configured to determine one or more parameters of the eye tissue based on the first return light.

In certain embodiments, a method is provided. The method includes receiving first source light generated from a hyperspectral illumination source. The first source light includes a plurality of wavelengths. The method also includes modulating each of the plurality of wavelengths of the first source light with a different frequency to generate second source light having a plurality of frequency modulated wavelengths. The method also includes transmitting the second source light to an optical fiber of an illumination device, so that the second source light in the optical fiber is emitted to illuminate an eye tissue. The method also includes selecting, with a first imaging device, at least a first frequency associated with a first frequency modulated wavelength of the plurality of frequency modulated wavelengths of the second source light. The method also includes capturing, with the first imaging device, first light returning from the eye tissue as a result of the first frequency modulated wavelength of the second source light contacting the eye tissue. The method further includes determining one or more parameters of the eye tissue based on the first return light.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, and may admit to other equally effective embodiments.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

Figure 1:
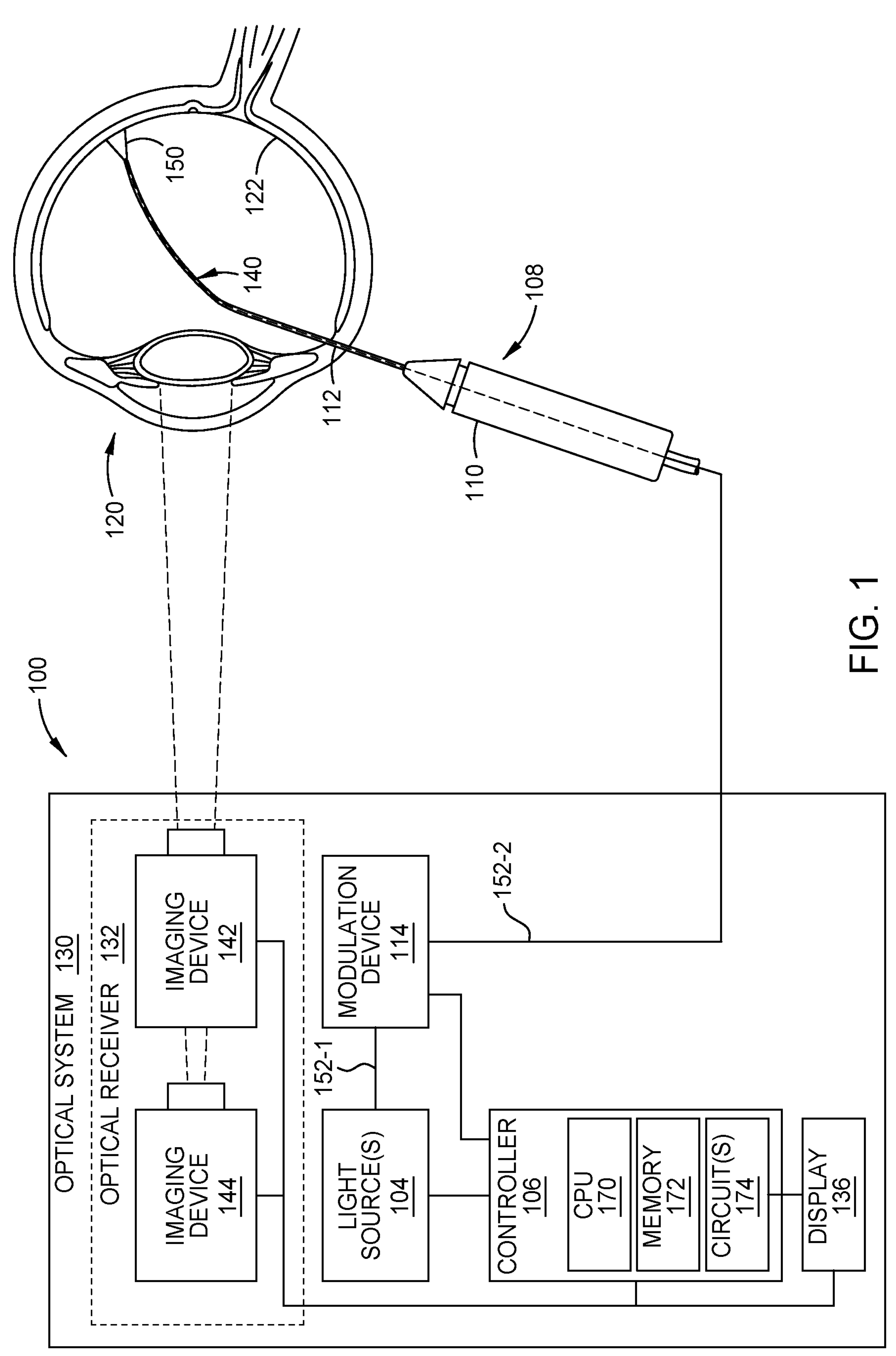
FIG. 1 illustrates an example system for obtaining ophthalmic information, according to certain embodiments.

Embodiments described herein provide optical systems, devices, and techniques for obtaining ophthalmic information with respect to a patient's eye during intraoperative ophthalmic procedures using multicolor endoillumination with hyperspectral imaging. The ophthalmic information can include, but is not limited to, parameters of eye tissues/structures related to treatments, parameters of eye tissues/structures related to disease states, topographical maps of various eye tissues/structures, etc. As used herein, the terms "information" and "data" may be used interchangeably to refer to qualitative observations and/or quantitative data.

An exemplary optical system described herein may include an illumination source and one or more imaging devices. An illumination device, such as an endo-illuminator, coupled to the illumination source may be inserted into a chamber (e.g., fundus) of the eye to illuminate a particular region or area of the eye within the chamber. For example, the illumination device may project illumination light (also referred to herein as "source light") onto a desired location/surface of the retina during a surgical procedure.

The imaging device(s) can be configured to receive light returning from an eye tissue/structure (also referred to herein as "return light" or "backward light") as a result of illumination light being projected onto a desired location/surface of the eye during the surgical procedure. For example, a first imaging device (e.g., microscope) may facilitate visualization of the desired location/surface of the eye. Additionally, a second imaging device (e.g., camera device, such as a hyperspectral (imaging) camera) may capture an image of the desired location/surface of the eye through a field-of-view (FOV) of the first imaging device.

In certain embodiments, the illumination device may project the illumination light across a range of wavelengths and at various different frequencies. For example, the optical system may modulate each wavelength of the illumination light with a different frequency, such that the illumination light projected on the desired location/surface of the eye includes multiple different wavelengths at different frequencies.

In certain embodiments, the second imaging device may capture an image of the target location/surface of the eye that is illuminated with multiple wavelengths of illumination light. For example, the second imaging device may lock-in to different modulated frequencies of the illumination light and capture an image of the target location/surface of the eye at the wavelength of the illumination light associated with the respective modulated frequency. Targeting particular modulated frequencies of the illumination light in this manner can improve the SNR of the target location/surface of the eye within the captured image.

In certain embodiments, the optical system may control a focus position (e.g., focal length) of the first imaging device, based on the different modulated frequencies being targeted by the second imaging device. Controlling the focus position of the first imaging device in this manner may reduce (or eliminate) chromatic aberrations caused by the multiple emitted wavelengths.

In certain embodiments, the optical system may determine ophthalmic information associated with various eye tissues/structures, based on the images captured using the techniques described herein. In some cases, the ophthalmic information may relate to one or more parameters of an eye tissue/structure that are used in disease diagnosis and/or stage evaluation, thereby providing additional data points to improve diagnostic accuracy. As a reference example, the optical system described herein may provide parameters (e.g., thickness) that may indicate an amount of wear, tearing, etc. of various eye tissues/structures that may be indicative of a disease and/or stage of a disease.

In some cases, the ophthalmic information may relate to one or more parameters of an eye tissue/structure, which may provide additional information to the surgeon regarding the eye tissue/structure, thereby improving the safety and/or effectiveness of a surgical procedure. As a reference example, certain ophthalmic surgical procedures, such as internal limiting membrane (ILM) removal and epiretinal membrane (ERM) removal, may involve a surgeon using forceps to grasp and separate (or peel) a first ocular tissue from a second ocular tissue without causing trauma to at least one of the tissues. In these surgical procedures, the optical system described herein may provide the surgeon with accurate information regarding the location, thickness and/or roughness of the ocular tissue(s). In certain embodiments, such information may be provided in the form of a topographical map of the ocular tissue(s). For example, the optical system may overlay the multiple images of the eye tissues/structures at the multiple wavelengths to generate the topographical map.

Note that while many of the following embodiments use thickness and roughness as reference examples of eye tissue parameters that may be determined using the optical system described herein, embodiments are not limited to such parameters and can include other types of parameters of eye tissues/structures. Further, as used herein, the term "return light" may include reflection, scattering, fluorescence, auto fluorescence, Raman spectra, or combinations thereof.

FIG. 1 illustrates a system 100 for obtaining ophthalmic information associated with a patient's eye, according to one embodiment. The system 100 includes an optical system 130 and an illumination device 108 (also referred to as probe) coupled to the optical system 130. The optical system 130 includes one or more light sources 104, a modulation device 114, a controller 106, an imaging device 142, and an imaging device 144.

The light source(s) 104 can generate laser light beams and/or illumination light beams that may be used during an ophthalmic procedure. For example, the light source(s) 104 may alternatively, sequentially, or simultaneously generate a laser light beam and an illumination light beam. A user, such as a surgeon or surgical staff member, may control the optical system 130 (e.g., via a foot switch, voice commands, etc.) to emit the laser light beam and/or the illumination light beam during an ophthalmic procedure, such as vitreoretinal surgery. In certain embodiments, optical system 130 includes a port, and the laser and/or illumination light beams may be emitted from the light source(s) 104, through the port, and into an optical fiber 152-2 partially housed inside illumination device 108.

The optical system 130 delivers the laser and/or illumination light beams from the port to illumination device 108 via optical fiber 152-2. As shown, illumination device 108 includes a hand-piece, or probe body, 110. Illumination device 108 also includes a tip 140 coupled to a distal end of hand-piece 110. Note that, herein, a distal end of a component refers to the end that is closer to a patient's body, or where the laser and/or illumination light is emitted out of the illumination device. On the other hand, the proximal end of the component refers to the end that is facing away from the patient's body or in proximity to, for example, the light source. Tip 140 includes a tube 112 extending an entire length of tip 140. In certain embodiments, tube 112 is a cylindrical hollow tube. Although not shown herein, optical fiber 152-2 extends an entire length of tube 112 to transmit laser and/or illumination light to the distal end of tube 112.

In operation, a surgeon uses hand-piece 110 to guide tube 112 into a patient's eye 120. Tube 112 is only partly inserted into eye 120 such that the proximal end of tube 112 is disposed outside eye 120. The light source(s) 104 generates a light beam 150, which is directed (or projected) by tube 112 to a desired location/surface of eye 120, such as retinal surface 122. In certain embodiments, illumination device 108 is an endoillumination device.

The light source(s) 104 may include a laser source (coherent light source) and/or an illumination source (incoherent light source). In certain embodiments, the illumination source includes a LED-based illuminator. In certain embodiments, the illumination source includes a broadband light source or hyperspectral light source. Hyperspectral light may refer to light beyond the visible spectrum including, for example, infrared and ultraviolet light. In certain embodiments, light source(s) 104 is integrated with a console (not shown). In some other embodiments, light source(s) 104 is a stand-alone light source.

The modulation device 114 is generally configured to perform frequency modulation of illumination light received from the light source(s) 104. In the embodiment shown in FIG. 1, the modulation device 114 is optically coupled to light source(s) 104 via optical fiber 152-1 and optically coupled to illumination device 108 via optical fiber 152-2. In certain other embodiments, modulation device 114 and light source(s) 104 may be coupled together through other configurations. In certain embodiments, the modulation device 14 modulates each wavelength of illumination light emitted from the light source(s) 104 with a different frequency. That is, the modulation device 114 receives one or more wavelengths of illumination light via optical fiber 152-1 and outputs one or more frequency modulated wavelengths of illumination light via optical fiber 152-2. In certain such embodiments, the light beam 150 directed onto the retinal surface 122 from tip 140 may include the one or more frequency modulated wavelengths of illumination light via the optical fiber 152-2.

Together, optical fibers 152 1-2 enable transmission of laser and/or illumination light from light source(s) 104 to illumination device 108. In certain embodiments, certain portions of optical fibers 152 may be disposed inside a cable. For example, a portion of optical fiber 152-2 located outside illumination device 108 may be disposed within an outer sleeve, whereas only the fiber without the outer sleeve is disposed inside illumination device 108. In certain embodiments, the modulation device 114 is an electro-optic modulator. The operation of the modulation device 114 may be controlled via controller 106, which is described in more detail below.

The system 100 uses optical fiber(s) 152 to transmit source light and uses free space transmission to return light. For example, the light beam 150 is directed onto the tissues/structures inside the eye (e.g., retinal surface 122) from tip 140, and the return light (e.g., at least a portion of the light reflected from the tissues/structures inside the eye) is collected by the imaging device 142 and the imaging device 144. The imaging device 142 (e.g., microscope) is generally configured to provide an enhanced view of the tissues/structures inside the eye. For example, the imaging device 142 can produce enlarged images (e.g., digital images) of the tissues/structures inside the eye, allowing an observer (e.g., surgeon) a closer view of the tissues/structures. In certain embodiments, a focus position (e.g., focal length) of the imaging device 142 is compensated based on one or more of the modulated frequencies of the emitted wavelengths of the illumination light. For example, the focus position may be adjusted (e.g., by the controller 106) in order to reduce (or eliminate) chromatic aberrations caused by the multiple wavelengths of reflected illumination light.

The imaging device 144 (e.g., hyperspectral camera) is generally configured to produce (e.g., capture) an image of the targeted tissues/structures inside the eye (e.g., retinal surface 122) based on the return light. In certain embodiments, the imaging device 144 is configured to select a particular modulated frequency of an emitted wavelength of the illumination light (e.g., light beam 150) and lock on to the selected modulated frequency. After locking on to the selected modulation frequency, the imaging device 144 can capture an image of the targeted tissues/structures at the wavelength of the illumination light associated with the selected modulation frequency. The input into the imaging device 144 is provided by the imaging device 142.

In certain embodiments, the operation of the imaging device 144 and the operation of the imaging device 142 may be synchronized (e.g., via the controller 106). For example, the controller 106 may trigger the imaging device 142 to adjust its focus position to the focal length associated with the modulation frequency locked on to by the imaging device 142. Once the focus position is adjusted, the controller 106 may trigger the imaging device 144 to capture an image of the targeted tissues/structures inside the eye through the FOV of the imaging device 142.

In certain embodiments, the imaging device 142 and the imaging device 144 may perform a time-based spectral sweep across one or more different wavelengths of different modulation frequencies. In these embodiments, the spectral sweep may be based on the shutter frequency of the imaging device 144.

Note that FIG. 1 illustrates a reference example of an optical system 130 and that, in other embodiments, the optical system 130 may have different configurations. For example, while FIG. 1 depicts the imaging devices 142, 144 and light source(s) 104 within the optical system 130, in some embodiments, the imaging devices 142, 144 and/or light source(s) 104 may be separate from the optical system 130. As a reference example, the light source(s) 104 may be included within a surgical console and the imaging devices 142, 144 may be part of a digital microscope. Further, note that while FIG. 1 depicts the imaging devices 142, 144 as separate devices, in some embodiments, the operations of the imaging devices 142, 144 may be implemented by a single device (depicted as optical receiver 132 in FIG. 1). For example, in certain embodiments, the optical receiver 132 is a digital microscope that includes optical components (e.g., an objective) and a digital camera to output an image.

Display 136 is coupled to controller 106 and imaging devices 144 and 142. Display 136 is capable of displaying to the surgeon ophthalmic information associated with the eye 120, including ophthalmic information obtained using illumination device 108 and imaging devices 142, 144. In the illustrated embodiment, display 136 is separate from imaging device 144 and the optical system 130. In some other embodiments, display 136 is integral with imaging device 144 or optical system 130. In certain embodiments, display 136 includes an augmented reality display. In certain embodiments, display 136 includes a virtual reality display.

In certain embodiments, display 136 includes a three-dimensional display to provide depth information to the surgeon. In certain embodiments, display 136 receives an image(s) captured by the imaging device 144 and presents the image(s) for viewing. In certain embodiments, display 136 receives information from the controller 106 and presents the information for viewing. Such information can include, for example, topographical information generated by the controller 106 based on image(s) captured by the imaging device 144.

Controller 106, such as a programmable computer, is generally configured to perform one or more operations described herein for generating (or obtaining) and displaying ophthalmic information associated with the eye 120. Controller 106 is coupled to one or more of light source(s) 104, imaging devices 142, 144, modulation device 114, and display 136. For example, controller 106 may control the operation of optical system 130 using a direct control of light source(s) 104, imaging devices 142, 144, modulation device 114, and/or display 136 or using indirect control of other controllers associated therewith. In operation, controller 106 may enable data acquisition and feedback from the respective components to coordinate operation of optical system 130.

Controller 106 includes a programmable central processing unit (CPU) 170, which is operable with a memory 172 (e.g., non-volatile memory) and support circuits 174. Support circuits 174 are conventionally coupled to CPU 170 and comprise cache, clock circuits, input/output subsystems, power supplies, and the like, and combinations thereof coupled to the various components of optical system 130.

In some embodiments, CPU 170 is one of any form of general purpose computer processor used in an industrial setting, such as a programmable logic controller (PLC), for controlling various monitoring system component and sub-processors. Memory 172, coupled to CPU 170, is typically one or more of readily available memory, including volatile or non-volatile memory. For example, memory 172 may be a random access memory (RAM), read only memory (ROM), floppy disk drive, hard disk, or any other form of digital storage, local or remote.

Herein, memory 172 stores instructions, that when executed by CPU 170, facilitates the operation of optical system 130. The instructions in memory 172 are in the form of a program product such as a program that implements the methods of the present disclosure (e.g., middleware application, equipment software application, etc.). In certain embodiments, optical systems disclosed herein are able to determine ophthalmic information (e.g., parameters, such as thickness, roughness, etc., associated with eye tissues/structures). In certain embodiments, optical systems disclosed herein are able to generate ophthalmic information (e.g., topographic information) based on images captured using one or more components (e.g., imaging devices 142, 144) of the optical system. Note that methods disclosed herein may be carried out using one or more of the optical system embodiments provided, and thus, optical system 130 is described in the following examples for illustrative purposes only.

Figure 2:
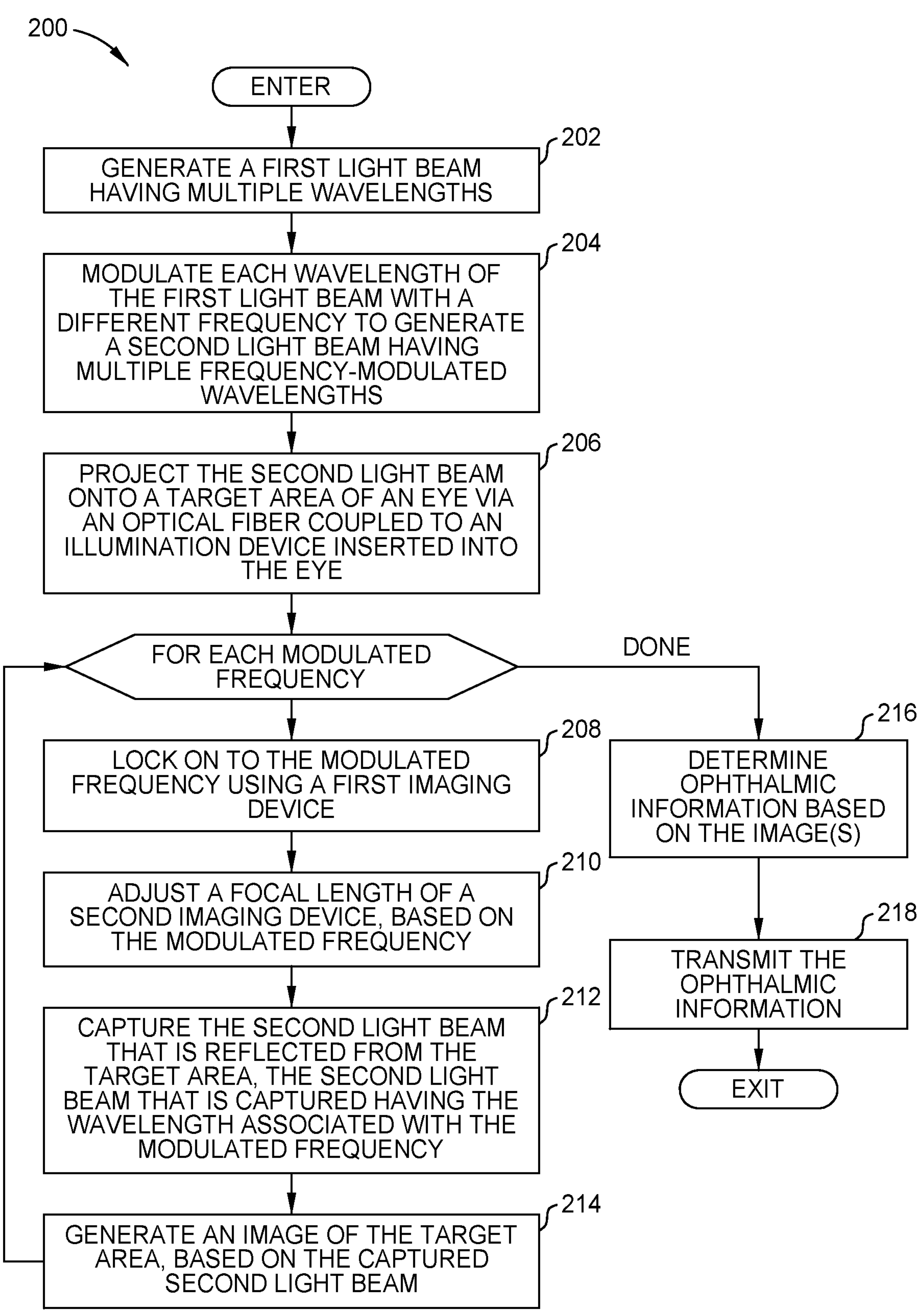
FIG. 2 is a flowchart of a method for obtaining ophthalmic information, according to certain embodiments.

FIG. 2 is a flowchart of a method 200 for obtaining ophthalmic information, according to one embodiment. The method 200 may be performed by one or more components of a system (e.g., system 100).

Method 200 enters at block 202, where the system generates a first light beam having multiple wavelengths. For example, the light source(s) 104 may generate and output a first light beam (e.g., illumination light) having multiple different wavelengths. As noted, in certain embodiments, the light source(s) 104 is a broadband light source. In certain embodiments, the light source(s) 104 is a hyperspectral light source. In these embodiments, the first light beam can include wavelengths in the visible light spectrum (e.g., approximately 380 to 750 nanometers (nm)), wavelengths in the near infrared spectrum (e.g., approximately 800 to 2,500 nm), and/or wavelengths in the mid infrared spectrum (e.g., approximately 0.8 to 1000 nm).

In certain embodiments, the wavelengths of the first light beam may be based on the eye tissue/structure that is being observed and/or interacted with. For example, different wavelengths of illumination light may have different penetration (or absorption) into the eye tissue/structure, depending on the particular wavelength. For instance, wavelengths between approximately 400 to 500 nm may allow for observing the superficial layers of the retina, the nerve fiber layer and internal limiting membrane, and the fluorescent retinal components (e.g., carotenoids of photoreceptor pigments acting as a yellowish filter in the macula, lipofuscin accumulated in the outer segments, and concentrates in the retinal pigment epithelium (RPE). Wavelengths between approximately 500 to 700 nm may allow for observing the retinal vascular layers and for discriminating between arteries and veins (oxygenated and deoxygenated blood). Here, the hemoglobin spectral signatures may provide both qualitative and quantitative oxygen saturation maps. This data can be used for monitoring retinal ischemia from either systemic diseases, such as diabetes, or from localized retinal arterial and vascular occlusions. Wavelengths beyond approximately 600 nm may allow for observing melanin, which is the dominant retinal pigment. Images at these wavelengths may enhance the visualization of retinal structures that contain this pigment, such as the underlying RPE. Wavelengths between approximately 732 to 865 nm may provide information about the oxygenation of the deepest retinal and superficial choroidal vasculature (CV). Wavelengths between approximately 955 to 1213 nm may allow for observing the choroid and sclera, congenital hypertrophy of the RPE, choroidal ruptures, and melanomas. In some cases, the lipids (or components of drusen) may show absorption peaks in the near infrared spectrum that exceed water absorption, and therefore images taken at longer wavelengths can be relevant in the study of age-related macular degeneration. Additionally or alternatively, in certain embodiments, the wavelengths of the first light may be based on the spectral sensitivity of the imaging device 144 (e.g., hyperspectral camera). For example, assuming the imaging device 144 can detect wavelengths ($\lambda$) between $\lambda_1$ and $\lambda_2$, where $\lambda_2 > \lambda_1$, then the wavelengths of the first light beam may be between $\lambda_1$ and $\lambda_2$.

At block 204, the system modulates each wavelength of the first light beam with a different frequency to generate a second light beam having multiple frequency-modulated wavelengths. For example, the modulation device 114 may receive the first light beam output from the light source(s) 104 and may output the second light beam with the frequency-modulated wavelengths. Each wavelength $\lambda_n$, of the first light beam may be set to a different modulation frequency $f_n$ to enable the system to recognize which wavelength is illuminated. This in turn enables the imaging device 144 to target particular wavelengths of interest, thereby improving SNR of targeted eye tissues/structures within captured image(s).

In certain embodiments, the set of frequencies that are used to modulate the different wavelengths may be based on one or more parameters of the imaging device 144 (e.g., hyperspectral camera). For example, the set of frequencies may be selected based on the shutter speed (or exposure time) of the imaging device 144. In one exemplary embodiment, the illumination modulation frequency may be larger than the frame rate of the imaging device 144 where the frame rate is based on the shutter time. In some embodiments, the turn on-time of the light source(s) 104 may be shorter than the frame time of the imaging device 144.

At block 206, the system projects the second light beam (having the multiple frequency-modulated wavelengths) onto a target area (e.g., retinal surface 122) of an eye (e.g., eye 120) via an optical fiber (e.g., optical fiber(s) 152) coupled to an illumination device (e.g., illumination device 108) inserted into the eye. In certain embodiments, the illumination device may be an endoilluminator that projects the multiple frequency-modulated wavelengths of the second light beam at the same time. In certain embodiments, the illumination device may be an endoilluminator that projects the multiple frequency-modulated wavelengths sequentially (e.g., one wavelength at each instance of time).

After block 206, the operations in blocks 208, 210, 212, and 214 are performed for each modulated frequency. At block 208, the system selects and locks on to the modulated frequency using a first imaging device (e.g., imaging device 144). In certain embodiments, the frequency selection may be based on an aperture of the imaging device 144 (e.g., the aperture of the imaging device 144 is inversely proportional to the shutter speed of the imaging device 144, and vice versa). In certain embodiments, the frequency selection may be based on spectral parameters of the targeted eye tissues/structures. For example, as noted above, different wavelengths may have different levels of penetration into particular eye tissues/structures.

Figure 3:
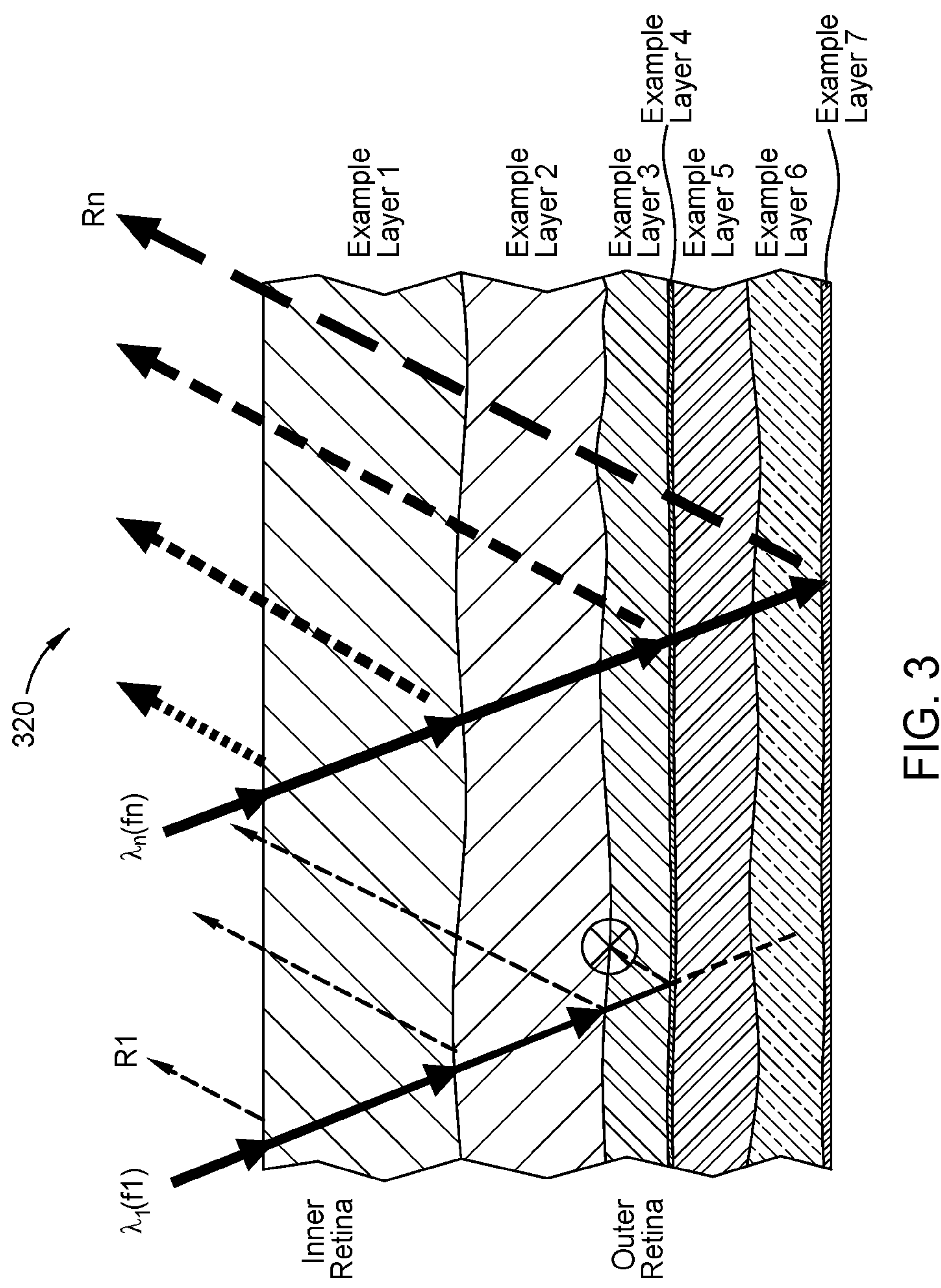
FIG. 3 illustrates example absorption of different illumination wavelengths into an eye tissue, according to certain embodiments.

As shown in FIG. 3, for example, different wavelengths of frequency-modulated wavelengths of light may have different amounts of absorption into tissue 320 and reflection off tissue 320, which includes multiple example layers 1-7. In certain embodiments, assuming tissue 320 is ocular (or eye) tissue, such as the retina, the example layer 1 may include the neural layers and blood vessels of the eye, the example layer 2 may include the photo receptors of the eye, the example layer 3 may include the RPE, the example layer 4 may include the Bruch's membrane, the example layer 5 may include the outer collagenous layer, the example layer 6 may include the choroid, and the example layer 7 may include the sclera. The inner retina region of the eye may include example layers 1-2, and the outer retina region of the eye may include example layers 3-7. Here, in particular, $\lambda_1(f_1)$ of the illumination light (e.g., "blue" illumination light) has a relatively short wavelength, is absorbed into the inner retina regions, and is reflected off as "$R_1$" from the inner retina regions. On the other hand, $\lambda_n(f_n)$ of the illumination light (e.g., "red" illumination light) has a relatively longer wavelength, is absorbed into the outer retina regions, and is reflected off as "$R_N$" from the outer retina regions. Thus, by locking to a known modulation frequency, the system can select a particular reflection layer of the target eye tissue/structure for viewing.

In certain embodiments, the first imaging device may lock-on to a selected (or specified) frequency-modulated wavelength of illumination by locking to the shutter frequency associated with the modulated frequency. For example, each modulated frequency that is used to modulate a different wavelength of illumination may have a corresponding (or associated) shutter frequency. In these embodiments, the first imaging device may perform a time sequence-based spectral sweep, locking-on to different modulated frequencies of interest by locking to the respective shutter frequencies.

Figure 4:
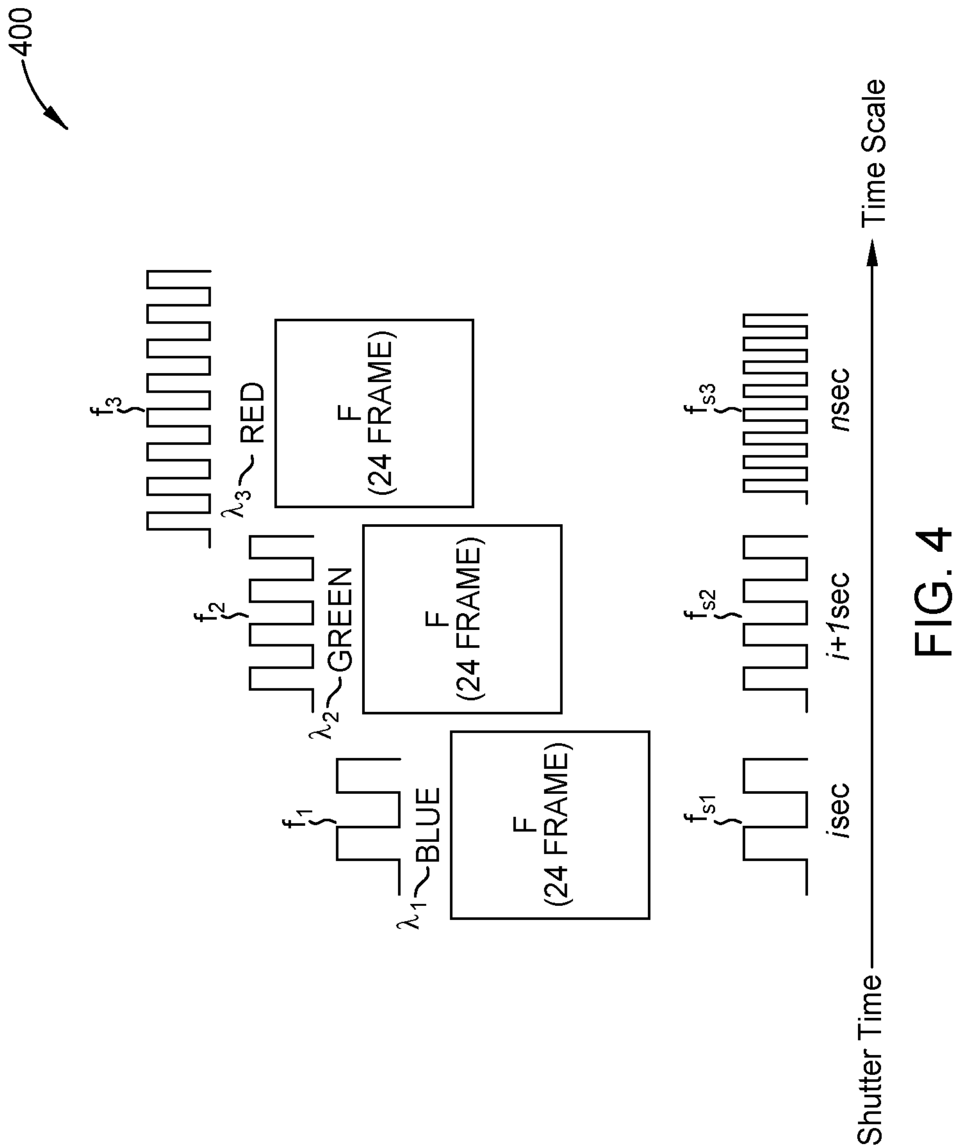
FIG. 4 illustrates an example timeline of an operation of an imaging camera, according to certain embodiments.

As shown in the timeline 400 of FIG. 4, for example, during a first amount of shutter time (e.g., i seconds of shutter time or X number of frames), the first imaging device may lock on to the modulated frequency ($f_1$) associated with a first wavelength of illumination ($\lambda_1$) by locking on to the shutter frequency ($f_{s1}$), during a subsequent second amount of shutter time, the first imaging device may lock on to the modulated frequency ($f_2$) associated with a second wavelength of illumination ($\lambda_2$) by locking on to the shutter frequency ($f_{s2}$), during a subsequent third amount of shutter time, the first imaging device may lock on to the modulated frequency ($f_3$) associated with a third wavelength of illumination ($\lambda_3$) by locking on to the shutter frequency ($f_{s3}$), and so on.

Referring back to FIG. 2, at block 210, the system adjusts a focal length of an objective lens of the second imaging device (e.g., imaging device 142), based on the modulated frequency. In certain embodiments, the second imaging device may be configured to sweep across multiple different focal lengths, where each focal length is associated with a different modulated frequency. The second imaging device may adjust the focal length of the objective lens to reduce chromatic aberrations that may be caused by the multiple wavelengths of the illumination light.

At block 212, the system captures the second light beam that is reflected from the target area (e.g., using imaging device 144). The reflected second light beam that is captured includes the wavelength associated with the modulated frequency and may not include wavelengths associated with the other modulated frequencies. At block 214, the system generates an image of the target area, based on the captured second light beam (e.g., using imaging device 144).

After an image has been captured for each frequency-modulated wavelength of illumination, the system determines ophthalmic information based on the image(s) (block 216). In certain embodiments, the ophthalmic information can include one or more parameters of the target area. For example, the system may determine a thickness and/or roughness of the target area (e.g., epiretinal membrane). In certain embodiments, assuming the imaging device 142 sweeps across two focal lengths, $FL(\lambda_1)$ and $FL(\lambda_2)$, the thickness (TT) of eye tissue/structure may be approximately equal to $A*(FL(\lambda_1)-FL(\lambda_2))$, where FL is the focal length of the imaging device 142 and A is a conversion coefficient. In some cases, $\lambda_1$ may be the lowest wavelength of interest and $\lambda_2$ may be the highest wavelength of interest. In certain embodiments, the ophthalmic information can allow for disease detection based on the spectral absorption images.

In certain embodiments, the system may generate topographical information (e.g., a topographical map) of the target area, based on the image(s). For example, the system (e.g., via controller 106) may overlay each image (corresponding to a different wavelength) to generate an image overlay with multiple wavelengths. This generated image overlay may be used as a topographical map of the target area within the eye.

At block 218, the system transmits the ophthalmic information. For example, the ophthalmic information may be transmitted to a display (e.g., display 136) for viewing in real-time by a surgeon performing an ophthalmic procedure. The method 200 may then exit.

Figure 5A:
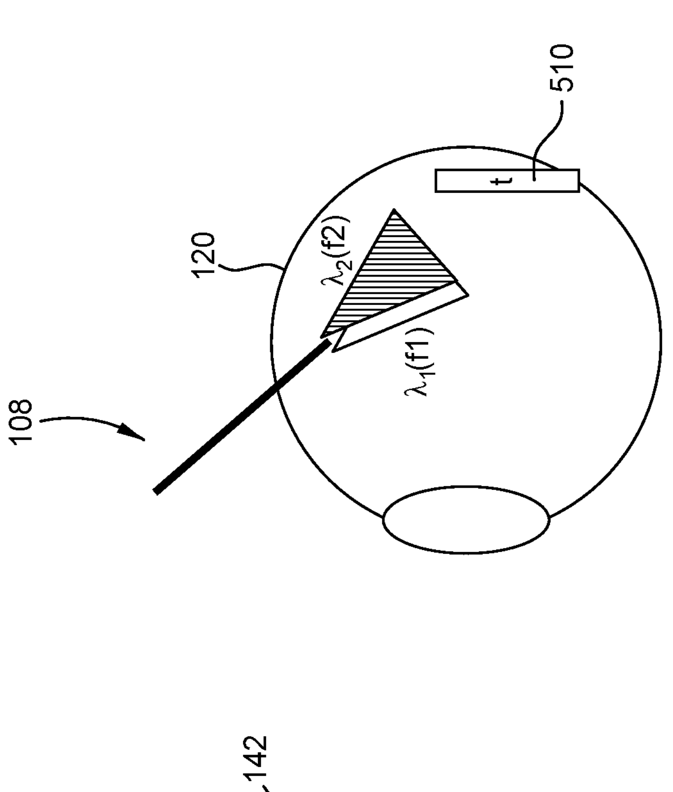
FIGS. 5A-5C illustrate an example sequence for obtaining ophthalmic information, according to certain embodiments.
Figure 5A:
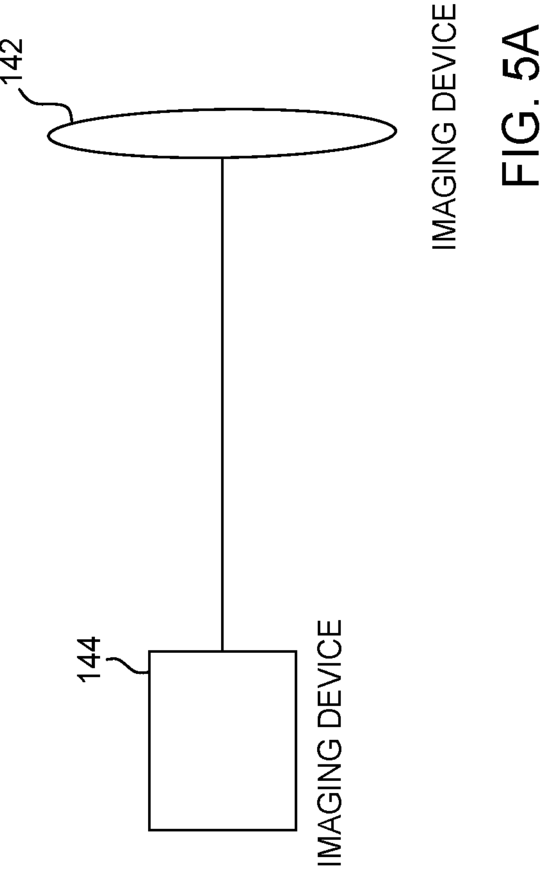
Figure 5B:
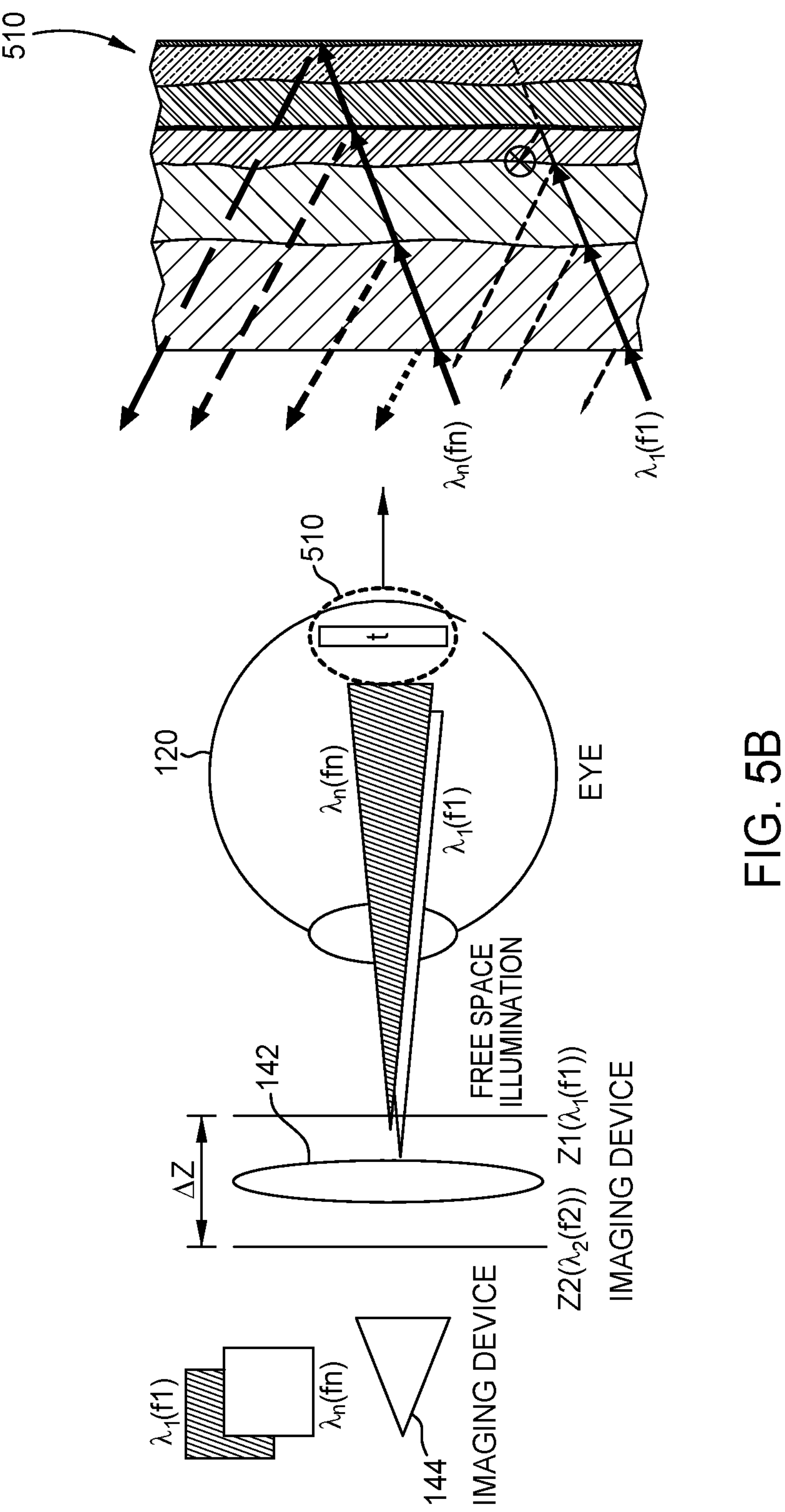
Figure 5C:
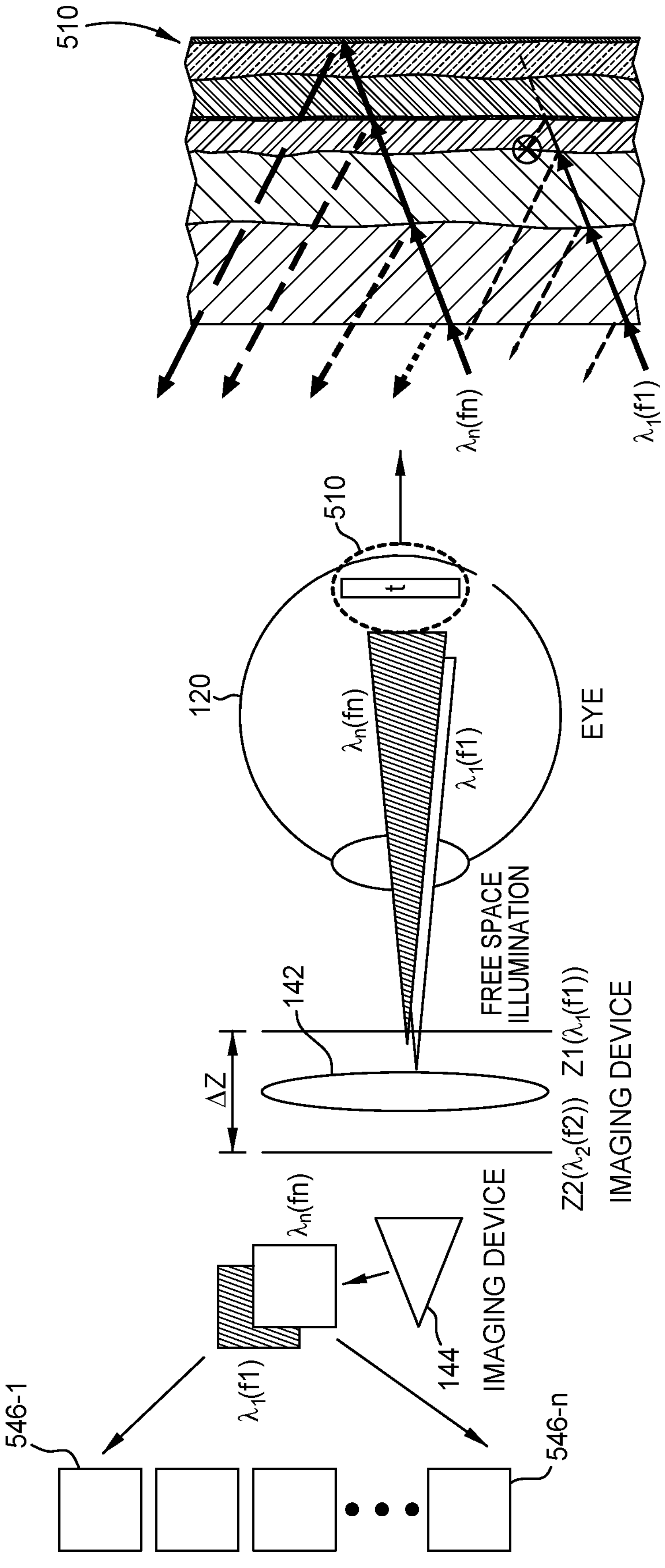

FIGS. 5A-5C illustrate an example sequence for obtaining ophthalmic information, according to one embodiment. As shown in FIG. 5A, an illumination light is projected onto tissue 510 within the eye 120 via the illumination device 108. The tissue 510 may be similar to the tissue 320 illustrated in FIG. 3. Here, the illumination light includes two frequency-modulated wavelengths, $\lambda_1(f_1)$ and $\lambda_n(f_2)$. That is, $\lambda_1$ of the illumination light is modulated with $f_1$ and $\lambda_2$ of the illumination light is modulated with $f_2$.

As shown in FIG. 5B, the projected illumination light is reflected off the tissue 510 through free space and is captured by the imaging devices 142, 144. Here, the imaging device 144 may sweep across the modulated frequencies $f_1$ and $f_2$, and capture a respective image of the tissue 510 having the wavelength ($\lambda_1$, $\lambda_2$) associated with the respective modulated frequency. At the same time, the imaging device 142 may sweep across different focal lengths ($\Delta Z$ between $Z2(\lambda_2(f_2))$ and $Z1(\lambda_n(f_2))$) and adjust the focal length of its objective mirror based on the modulated frequency that is targeted by the imaging device 144.

As shown in FIG. 5C, the captured images 546-1 and **546-*n* of the tissue 510 may be overlaid to generate an image overlay that indicates topographical information of the tissue 510**.

In summary, embodiments of the present disclosure enable the acquisition of ophthalmic information during ophthalmic procedures using an optical system based on endoillumination with hyperspectral imaging. Optical systems and/or methods described herein are particularly advantageous for improving the safety and/or effectiveness of surgical procedures and/or for providing additional data points to improve diagnostic accuracy.

As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiples of the same element (e.g., a-a, a-a-a, a-a-b, a-a-c, a-b-b, a c c, b-b, b-b-b, b-b-c, c-c, and c-c-c or any other ordering of a, b, and c).

The foregoing description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with the language of the claims.

Within a claim, reference to an element in the singular is not intended to mean "one and only one" unless specifically so stated, but rather "one or more." Unless specifically stated otherwise, the term "some" refers to one or more. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112(f) unless the element is expressly recited using the phrase "means for" or, in the case of a method claim, the element is recited using the phrase "step for." The word "exemplary" is used herein to mean "serving as an example, instance, or illustration." Any aspect described herein as "exemplary" is not necessarily to be construed as preferred or advantageous over other aspects.

What is claimed is:

1. A system, comprising:

an endoillumination device comprising an optical fiber configured to be inserted into a chamber of an eye;

a hyperspectral illumination source;

a controller;

a modulation device coupled to each of the endoillumination device, the hyperspectral illumination source, and the controller, wherein the modulation device is configured to:

receive first source light generated from the hyperspectral illumination source, the first source light comprising a plurality of wavelengths;

modulate each of the plurality of wavelengths of the first source light with a different frequency to generate second source light having a plurality of frequency modulated wavelengths; and transmit the second source light to the optical fiber, wherein the optical fiber is configured to emit the second source light in the optical fiber from the endoillumination device to illuminate an eye tissue within the chamber of the eye; and a first imaging device configured to:

select at least a first frequency associated with a first frequency modulated wavelength of the plurality of frequency modulated wavelengths of the second source light; and capture first light returning from the eye tissue as a result of the first frequency modulated wavelength of the second source light contacting the eye tissue, a second imaging device comprising an objective lens, the second imaging device configured to:

adjust a focal length of the objective lens based on the first frequency associated with the first frequency modulated wavelength;

wherein the controller is configured to determine one or more parameters of the eye tissue based on the first return light.

2. The system of claim 1, the second imaging device further configured to:

generate an enlarged image of the eye tissue based on the first return light passing through the objective lens with the adjusted focal length.

3. The system of claim 2, wherein the first imaging device is configured to capture the first return light after the first return light has passed through the second imaging device.

4. The system of claim 1, wherein the first frequency associated with the first frequency modulated wavelength is selected based on at least one of: (i) one or more parameters of the first imaging device, (ii) a target reflection layer of the eye tissue, (iii) or a wavelength associated with the first frequency modulated wavelength.

5. The system of claim 4, wherein the one or more parameters of the first imaging device comprises at least one of: (i) a shutter frequency, (ii) a frame time, or (iii) an aperture.

6. The system of claim 1, wherein the first imaging device is further configured to lock on to the selected first frequency associated with the first frequency modulated wavelength prior to capturing the first return light.

7. The system of claim 6, wherein the first imaging device is configured to lock on to the selected first frequency associated with the first frequency by locking on to a shutter frequency associated with the selected first frequency.

8. The system of claim 1, wherein the one or more parameters of the eye tissue comprises at least one of (i) a thickness or (ii) a roughness.

9. The system of claim 1, wherein the first imaging device is further configured to:

select at least a second frequency associated with a second frequency modulated wavelength of the plurality of frequency modulated wavelengths of the second source light; and capture second light returning from the eye tissue as a result of the second frequency modulated wavelength of the second source light contacting the eye tissue.

10. The system of claim 9, wherein the first imaging device is further configured to:

generate a first image of the eye tissue, based on the first return light; and generate a second image of the eye tissue, based on the second return light.

11. The system of claim 10, wherein the controller is configured to generate topographical information associated with the eye tissue, based on the first image and the second image.

12. The system of claim 11, wherein the topographical information comprises an image overlay of the first image with the second image.

13. The system of claim 1, wherein the first imaging device is a hyperspectral imaging camera.

14. A method of operating an optical system comprising:

receiving first source light generated from a hyperspectral illumination source, the first source light comprising a plurality of wavelengths;

modulating each of the plurality of wavelengths of the first source light with a different frequency to generate second source light having a plurality of frequency modulated wavelengths;

transmitting the second source light to an optical fiber of an endoillumination device, so that the second source light in the optical fiber is emitted to illuminate an eye tissue within a chamber of the eye;

selecting, with a first imaging device, at least a first frequency associated with a first frequency modulated wavelength of the plurality of frequency modulated wavelengths of the second source light;

capturing, with the first imaging device, first light returning from the eye tissue as a result of the first frequency modulated wavelength of the second source light contacting the eye tissue;

adjusting a focal length of an objective lens of a second imaging device based on the first frequency associated with the first frequency modulated wavelength; and determining one or more parameters of the eye tissue based on the first return light.

15. The method of claim 14, further comprising:

generating, with the second imaging device, an enlarged image of the eye tissue based on the first return light passing through the objective lens with the adjusted focal length.

16. The method of claim 15, wherein the first light returning from the eye tissue is captured with the first imaging device after the first return light has passed through the second imaging device.

17. The method of claim 14, wherein the first frequency associated with the first frequency modulated wavelength is selected based on at least one of: (i) one or more parameters of the first imaging device, (ii) a target reflection layer of the eye tissue, (iii) or a wavelength associated with the first frequency modulated wavelength.

18. The method of claim 17, wherein the one or more parameters of the first imaging device comprises at least one of: (i) a shutter frequency, (ii) a frame time, or (iii) an aperture.

19. The method of claim 14, further comprising locking on, with the first imaging device, to the selected first frequency associated with the first frequency modulated wavelength prior to capturing the first return light.

20. The method of claim 19, wherein locking on to the selected first frequency associated with the first frequency comprises locking on to a shutter frequency associated with the selected first frequency.

* * * * *